(12) United States Patent
Uludağ et al.

(10) Patent No.: US 10,067,083 B2
(45) Date of Patent: Sep. 4, 2018

(54) ELECTROCHEMICAL SENSOR ARRAY AND APPARATUS

(71) Applicant: TUBITAK, Ankara (TR)

(72) Inventors: Yildiz Uludağ, Kocaeli (TR); Mahmut Şamil Sağiroğlu, Kocaeli (TR); Aylin Ersoy, Kocaeli (TR); Edis Ardinç, Kocaeli (TR); Sinan Budak, Kocaeli (TR); Atike Demīralp, Kocaeli (TR); Halit Hakan Efe, Kocaeli (TR)

(73) Assignee: TUBITAK, Ankara (TR)

( * ) Notice: Subject to any disclaimer, the term of this patent is extended or adjusted under 35 U.S.C. 154(b) by 0 days.

(21) Appl. No.: 15/302,557

(22) PCT Filed: Apr. 6, 2015

(86) PCT No.: PCT/IB2015/052479
§ 371 (c)(1),
(2) Date: Oct. 7, 2016

(87) PCT Pub. No.: WO2015/155665
PCT Pub. Date: Oct. 15, 2015

(65) Prior Publication Data
US 2017/0030855 A1    Feb. 2, 2017

(30) Foreign Application Priority Data
Apr. 7, 2014   (TR) .............................. a 2014 03992

(51) Int. Cl.
*G01N 27/327* (2006.01)
*B01L 3/00* (2006.01)
*G01N 27/27* (2006.01)

(52) U.S. Cl.
CPC .......... *G01N 27/3276* (2013.01); *B01L 3/502* (2013.01); *B01L 3/502715* (2013.01);
(Continued)

(58) Field of Classification Search
None
See application file for complete search history.

(56) References Cited

U.S. PATENT DOCUMENTS

| | | | |
|---|---|---|---|
| 4,655,880 A * | 4/1987 | Liu ...................... | A61B 5/1486 204/403.1 |
| 5,520,787 A * | 5/1996 | Hanagan ............... | B01L 3/5027 204/403.14 |

(Continued)

FOREIGN PATENT DOCUMENTS

| | | |
|---|---|---|
| WO | WO2008127269 | 10/2008 |
| WO | WO2008154416 A2 | 12/2008 |

OTHER PUBLICATIONS

Olcer et al. (Biosensors and Bioelectronics 62, 2014, 163-169, NPL Nov. 24, 2016, 7 pages).*

(Continued)

*Primary Examiner* — Gurpreet Kaur
*Assistant Examiner* — Steven Eric Rosenwald
(74) *Attorney, Agent, or Firm* — Gokalp Bayramoglu

(57) ABSTRACT

This invention relates to an apparatus suitable to be used for analyzing at least one sample with an electrochemical sensor array, comprising at least one upper layer; at least one inlet and at least one outlet opening provided on the upper layer; at least one lower layer having at least one recess thereon; at least one two-sided adhesive membrane matching to the recess; at least one sensor array secured to the lower layer, at least one reference electrode, at least one counter electrode, at least one communication channel, at least one conductive line providing a connection between the working electrode and the communication channel on at least one plate; at least one further two-sided adhesive membrane spaced from the adhesive membrane positioned on the lower layer and enabling the sensor array to be secured to the upper layer.

18 Claims, 4 Drawing Sheets

(52) U.S. Cl.
CPC ...... *G01N 27/27* (2013.01); *B01L 2300/0645* (2013.01); *B01L 2300/0809* (2013.01); *B01L 2300/0877* (2013.01); *B01L 2300/0887* (2013.01)

(56) References Cited

U.S. PATENT DOCUMENTS

| | | | | |
|---|---|---|---|---|
| 8,329,010 | B2* | 12/2012 | Gau | G01N 33/5438 204/403.01 |
| 8,834,690 | B2* | 9/2014 | Ghesquiere | C12Q 1/001 204/401 |
| 2003/0148342 | A1* | 8/2003 | Gau | B01L 3/502715 435/6.11 |
| 2005/0268701 | A1* | 12/2005 | Hintsche | G01N 27/403 73/53.01 |
| 2006/0019273 | A1* | 1/2006 | Connolly | B01L 3/502715 435/6.11 |
| 2008/0182136 | A1 | 7/2008 | Arnold et al. | |
| 2010/0301398 | A1 | 12/2010 | Rothberg et al. | |
| 2011/0286888 | A1* | 11/2011 | Barlag | G01N 27/403 422/82.01 |

OTHER PUBLICATIONS

Yildiz Uludag et al., "Design and characterisation of a thin-film electrode array with shared reference/counter electrodes for electrochemical detection", Biosensors and Bioelectronics, vol. 57, Feb. 1, 2014, pp. 85-90, XP055202463, ISSN: 0956-5663, DOI: 10.1016/jbios.2014.01.048 p. 86, col. 2, paragraph 2; figure 1 p. 87, col. 2, paragrapph 5-p. 88, col. 2, paragraph 1 p. 89, col. 2, paragraph 2-p. 90, col. 1, paragraph 2.

Zehra Olcer et al., "Fast and sensitive detection of mycotoxins in wheat using microfluidics based Real-time Electrochemical Profiling", Biosensors and Bioelectronics, vol. 62, Jun. 18, 2014, pp. 163-169, XP055202464, ISSN: 0956-5663, DOI: 10.1016/j.bios.2014.06.025 p. 164, col. 1, paragraph 3-col. 2, paragraph 1 p. 164, col. 2, paragraph 4; figure 1 p. 168, col. 2, paragraph 3.

Pablo Fanjul-Bolado et al., "Amperometric detection in TMB/HRP-based assays", Analytical and Bioanalytical Chemistry, Springer, Berlin, DE, vol. 382, No. 2, May 1, 2005, pp. 297-302, XP019327343, ISSN: 1618-2650, DOI: 10.1007/S00216-005-3084-9 p. 298, col. 2, paragraph 3-4; figure 1.

* cited by examiner

ELECTROCHEMICAL SENSOR ARRAY AND APPARATUS

CROSS REFERENCE TO RELATED APPLICATIONS

This application is the national phase entry of International Application No. PCT/IB2015/052479, filed on Apr. 6, 2015, which is based upon and claims priority to TR 2014/03992, filed on Apr. 7, 2014, the entire contents of which are incorporated herein by reference.

TECHNICAL FIELD

This invention relates to an electrochemical sensor array and apparatus for analyzing a sample.

BACKGROUND

Electrochemical sensors are analytical devices comprising a biological diagnosis element and a suitable convertor. The convertor converts chemical change resulting from an interaction between molecules and a receptor into an output signal. The receptor agent can be an enzyme, a microorganism, a tissue or an antibody, a nucleic acid or a bio-ligand that can be a synthetic detector. The main application areas are quality control procedures in agriculture food and pharmaceutics industry, biological war agents causing environmental pollution and medical diagnosis methods. Diagnosis applications are bio-indicators available in the human body fluids, such as metabolites, proteins or nucleic acids which are related to a disease. The concentration of a bio-indicator in the body fluids is used to determine the type, condition or progress of a disease as well as the response of the patient to the treatment. In the market, there are a great variety of electrochemical sensors such as blood sugar, cholesterol, uric acid and lactic acid biosensors. Blood sugar biosensors used by the diabetic patients are the most common biosensors.

Electrochemical biosensors mainly comprise a working electrode modified with biological identification agent, a reference electrode and a counter electrode. Typically, electrodes are placed on a planar surface with a tool used for carrying fluid sample/reaction agents. Electrochemical sensors comprise a batch electrode (working, reference or counter) for measuring an analyte (sample) or an electrode series for multiple analyte measurements. Typical measurement technique is a flow sensitive measurement technique, which is performed by measuring a voltage generated by an enzyme, due to a biochemical reaction, using an electrochemical device.

Measurement of analytes with an electrochemical sensor array requires a tool for carrying the fluid into the sensor array for analysis purposes. To this end, in order to carry the fluid within the sensor array, an apparatus can be designed that is capable of establishing a proper connection with the electrodes and that can be mounted to and released from the device in an easy manner. For disposable sensors, such apparatus should not be expensive and should be easily manufactured. The flow cell provided in the apparatus must be small so that a lower amount of sample is used, and must allow a uniform distribution of fluid to all electrodes. In order to increase diffuse of analytes around the electrodes and to reduce mass transfer effects, it is preferred that the distance between the electrodes and the upper wall of the flow cell is small.

International patent document WO2008/154416, as part of the state-of-art, describes electrochemical biosensors and arrays. The inventive device comprises a structural body or layer. The body comprises a lower or bottom layer, an intermediate layer or a binding layer and an upper layer. Inside the body, there is a reservoir. The device also comprises a working electrode, a reference electrode and an auxiliary electrode. The working electrode and reference electrode are located in the reservoir whereas the auxiliary electrode is located outside the reservoir. A cover for reservoir surrounds the opening inside the reservoir. The device also comprises a sensor chemical inside the reservoir. The sensor chemical may be an enzyme or one or more polymer layers.

In international patent document WO2008/127269 the apparatus comprises a support body comprising a receiving surface and a receiving substrate. The support body comprises a mesa located within a recessed area. The fluid cell structure has a silicone or similar elastomer compressible layer around the mesa. The depth of the recessed area less the height of the mesa is the height of the interior volume of the fluidic cell once the plastic support body and planar substrate are secured together. This height is carefully measured to achieve the appropriate fluidic cell height to optimize fluid flow versus mass transfer conditions for the intended biochemical assay application. Fluidic inlet and outlet ports are drilled in the mesa for the attachment of external tubing.

US2008/0182136 describes an electrochemical cell with a micro scale and method for incorporating the cell. An electrochemical cell for processing a sample fluid has a body with a flow path. The flow path comprises an inlet and an outlet. The cell also comprises a reference electrode, a counter electrode in fluid communication with the flow path and a working electrode in fluid communication with the flow path. In an embodiment of the document, the invention comprises a body having a cell fluid manifold. The manifold has a primary flow path through which a sample fluid passes. The flow path has an inlet and an outlet, and is in fluid communication with at least two secondary conduits.

SUMMARY OF THE INVENTION

An object of this invention is to provide a sensor array and apparatus wherein the interaction between the electrodes is minimized.

Another object of this invention is to provide a sensor array and apparatus wherein all the electrodes provide same electrochemical reaction.

A further object of this invention is to provide a sensor array and apparatus wherein a lower amount of sample is used, and which is easy to implement, and cost effective.

BRIEF DESCRIPTION OF THE DRAWINGS

A "sensor array and apparatus" provided for purposes of achieving the object of the invention is illustrated in the accompanying drawings, in which.

Figure 1:
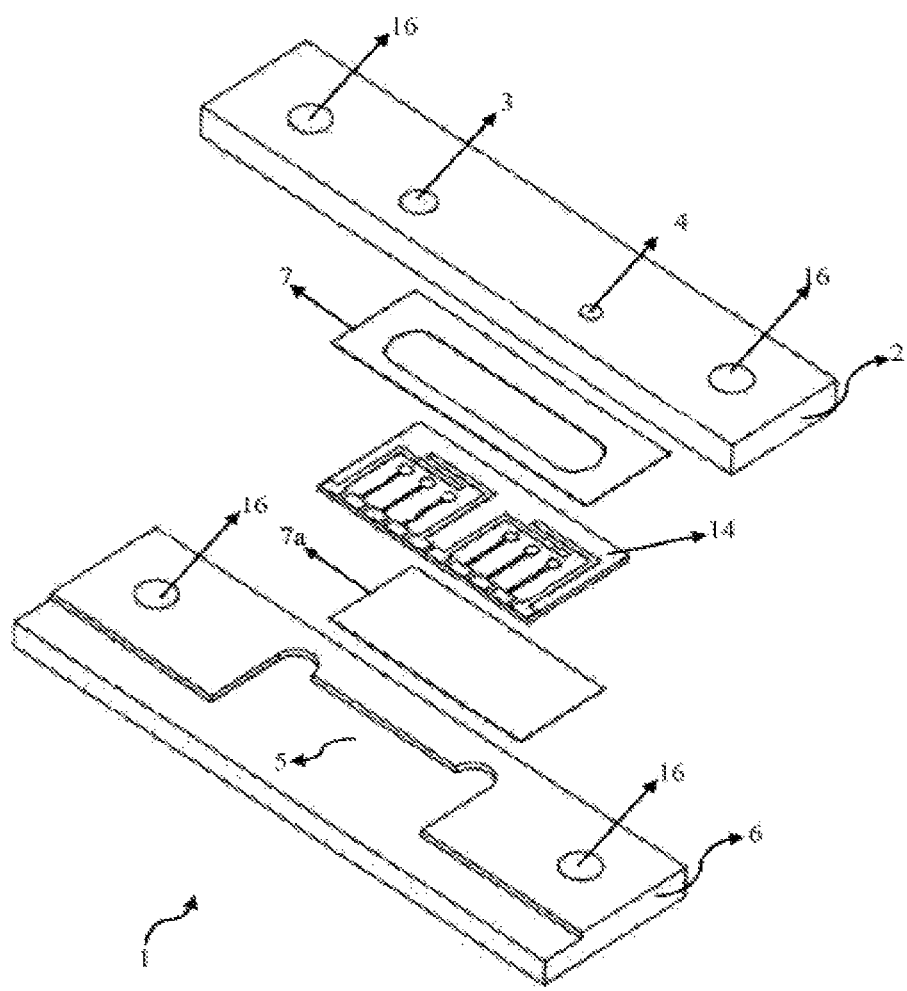
FIG. 1 is a perspective view of the disassembled inventive apparatus.

All the parts illustrated in the drawings are individually assigned a reference numeral and the corresponding terms of these numbers are listed as follows.

1. Apparatus
2. Upper layer
3. Inlet opening
4. Outlet opening
5. Recess
6. Lower layer
7, 7a. Adhesive membrane
8. Working electrode
9. Reference electrode
10 Counter electrode
11 Communication channel
12. Conductive line
13. Plate
14. Sensor array
15. Flow channel

DETAILED DESCRIPTION OF THE EMBODIMENTS

Figure 2:
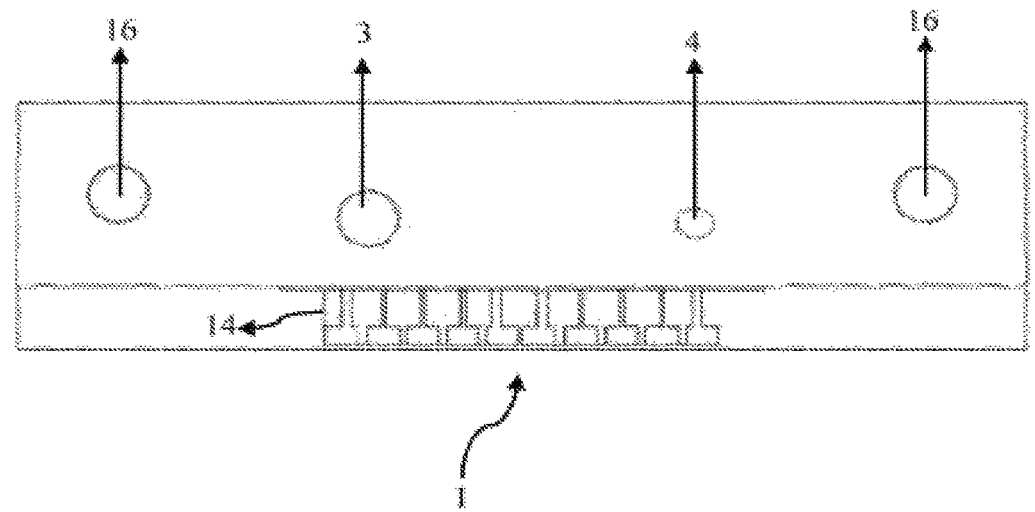
FIG. 2 is a plan view of the inventive apparatus.
Figure 3:
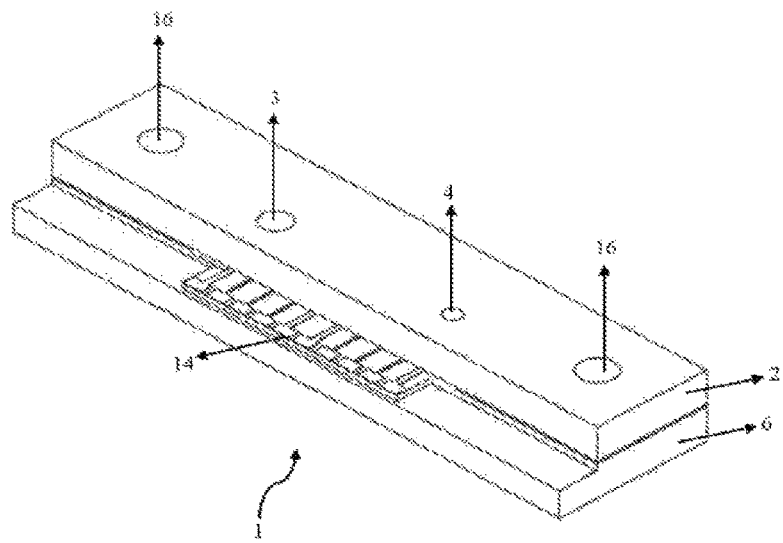
FIG. 3 is a perspective view of the inventive apparatus.
Figure 4:
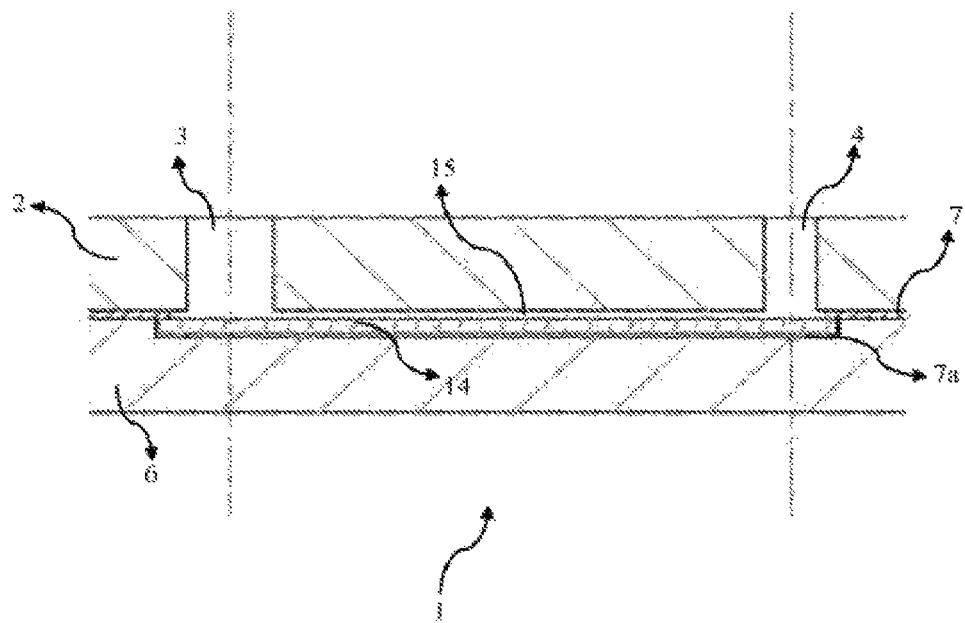
FIG. 4 is a sectional view of a flow channel of the inventive apparatus.
Figure 5:
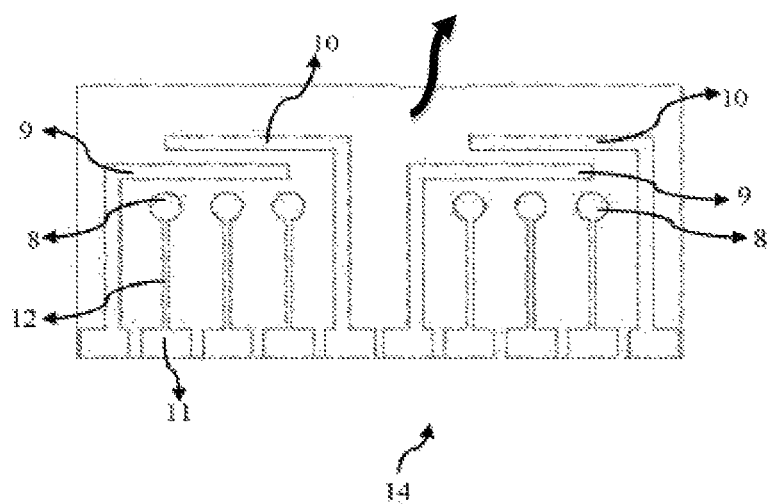
FIG. 5 is a view of the electrodes contained in the sensor array of the inventive apparatus.
Figure 6:
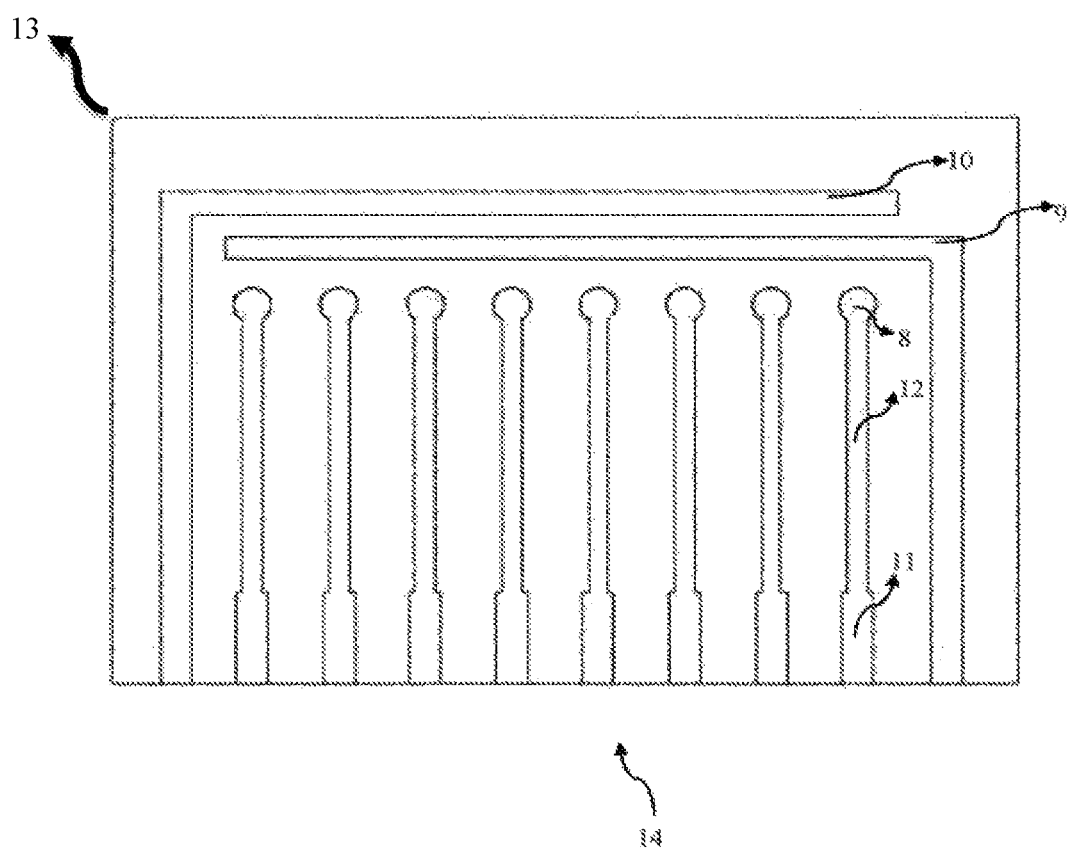
FIG. 6 is another view of the electrodes contained in the sensor array of the inventive apparatus.

Apparatus (1), as illustrated in FIGS. 1-5, which is suitable to be used for analyzing at least one sample with an electrochemical sensor array comprises:

at least one upper layer (2);

at least one inlet (3) and at least one outlet opening (4) provided on the upper layer;

at least one lower layer (6) with at least one recess (5) thereon;

at least one two-sided adhesive membrane (7a) matching to recess (5) on lower layer (6), at least one sensor array (14) secured to lower layer (6) by means of adhesive membrane (7a) composed of positioning at least one working electrode (8), at least one reference electrode (9), at least one counter electrode (10), at least one communication channel (11), at least one conductive line (12) providing a connection between working electrode (8) and communication channel (11) on at least one plate (13);

at least one measuring device (not shown) associated with communication channel (11);

at least one further two-sided adhesive membrane (7) spaced from adhesive membrane (7) positioned on lower layer (6) and enabling sensor array (14) to be secured to upper layer (2), and at least one flow channel (15) formed as a result of the space between adhesive membranes (7, 7a) and associated with inlet (3) and outlet openings (4) located on upper layer (2) for carrying the sample.

In the present invention, the sample to be analyzed is fed to flow channel (15) through inlet opening (3). The sample moving along flow channel (15) contacts to working (8), reference (9) and counter electrodes (10) throughout the analysis. A current is generated on working electrode (8) modified with a recognizing agent (such as a protein, nucleic acid, antibody, enzyme or synthetic receptor) suitable for the substance to be analyzed, due to the reaction resulting from the interaction between the recognizing agent and sample, and the current generated is transferred to communication channel (11) by conductive line (12). Communication channel (11) does not contact to the sample and transfers the current resulting from the reaction to the measuring device. Based on the current value read by the measuring device, analysis of the sample is performed. At the end of the analysis, the sample reaches to outlet opening (4) so that it is removed from apparatus (1).

In an embodiment of the invention, plate (13) is made of glass, silicon dioxide or ceramic; electrodes (8, 9, 10) are made of gold, titanium, platinum, chromium or aluminum oxide whereas upper (2) and/or lower layer (6) is made of plastic.

In another embodiment of the invention, three working electrodes (8) are positioned on plate (13) whereas eight working electrodes (8) are positioned thereon in a further embodiment In a preferred embodiment of the invention, each working electrode is positioned distanced from the other working electrodes so as the working electrodes do not interact with each other. Throughout the analysis, reference electrode (9), counter electrode (10) and working electrode (8) are aligned in order to receive same electrochemical reaction from all the electrodes.

In an illustrative embodiment of the invention, the size of upper layer (2) of apparatus (1) is smaller than that of lower layer (6) to allow conductive line (12) not to be covered and to connect it to the measuring device.

In an alternative embodiment of the invention, reference (9) and counter electrodes (10) are rectangle. In this embodiment, the reference and the counter electrodes (9, 10) are positioned on plate (13) such that they surround working electrode (8).

In another embodiment of the invention, upper layer (2) and lower layer (6) comprise at least one hole (16) matching to each other so that upper layer (2) is reliably secured to lower layer (6) by means of at least one connecting member (not shown).

In another embodiment of the invention, the diameter of working electrode (8) is larger than the width of conductive line (12).

Thanks to the co-operation of reference (9) and counter electrodes of apparatus (1) according to the invention with working electrode (8), the detection area is rendered small and thus the size of flow channel (15) is reduced. Thus, cost of production is reduced while at the same time it is made possible that a smaller amount of sample is used. Moreover, due to the alignment of all electrodes (8, 9, 10), same electrochemical reaction is received from the electrodes, thereby obtaining a more accurate analysis result.

Within the main concepts given herein, various embodiments of "An Electrochemical Sensor Array and Apparatus", being the object of the invention, can be designed; and the invention is not limited to the embodiments disclosed herein, the scope of which is defined by the following claims.

What is claimed is:

1. An apparatus having an electrochemical sensor array for analyzing a sample comprising:
    at least one upper layer;
    at least one inlet opening and at least one outlet opening, wherein the inlet opening and the outlet opening are arranged on the upper layer;
    at least one lower layer having a recess thereon;
    at least one first two-sided adhesive membrane matching to the recess on the lower layer;
    at least one sensor array secured to the lower layer and embedded within the recess through the first two-sided adhesive membrane, wherein the sensor array includes at least one working electrode, at least one reference electrode, at least one counter electrode, at least one communication channel, and at least one conductive line, wherein the conductive line provides a connection between the working electrode and the communication channel; wherein the working electrode, the reference electrode, and the counter electrode are integrally formed on an upper surface of a plate;

at least one measuring device associated with the communication channel;

at least one second two-sided adhesive membrane spaced from the first two-sided adhesive membrane, wherein the second two-sided adhesive membrane is provided between the sensor array and the lower layer, such that the sensor array is secured to the upper layer, the second two-sided adhesive membrane is placed adjacent to the upper layer and is provided with an opening;

at least one flow channel formed between the upper layer and the sensor array as a result of the opening wherein the flow channel is associated with the inlet opening and the outlet opening located on the upper layer for carrying the sample.

2. The apparatus according to claim 1, wherein the plate is made of glass, silicon dioxide or ceramic.

3. The apparatus according to claim 1, wherein each of the working electrode, the reference electrode, and the counter electrode is made of gold, titanium, platinum, chromium or aluminum.

4. The apparatus according to claim 1, wherein each of the upper layer and the lower layer is made of plastic.

5. The apparatus according to claim 1, wherein three working electrodes are arranged on the plate.

6. The apparatus according to claim 1, wherein a plurality of working electrodes are arranged on the plate.

7. The apparatus according to claim 1, wherein a plurality of working electrodes are arranged on the plate, and the plurality of working electrodes are spaced from each other.

8. The apparatus according to claim 7, wherein the reference electrode, the counter electrode and the working electrode are aligned in order to receive a same electrochemical reaction from each working electrode throughout an analysis.

9. The apparatus according to claim 1, wherein the upper layer has a size smaller than that of the lower layer to allow the conductive line not to be covered and to connect the conductive line to the measuring device.

10. The apparatus according to claim 1, wherein the reference electrode and the counter electrode form a rectangular enclosure around the working electrodes.

11. The apparatus according to claim 10, wherein the reference electrode and the counter electrode are L-shaped and positioned in two opposite sides of the working electrodes, wherein a lateral line of L-shaped reference electrode extends toward the counter electrode, a lateral line of the L-shaped counter electrode extends toward the reference electrode, and the lateral line of the L-shaped counter electrode is located above and covers a part of the lateral line of L-shaped reference electrode.

12. The apparatus according to claim 1, wherein each of the upper layer and the lower layer comprises at least one hole matching to each other so that the upper layer is reliably secured to the lower layer through at least one connecting member.

13. The apparatus according to claim 1, wherein the working electrode has a diameter larger than the width of the conductive line.

14. The apparatus according to claim 2, wherein the working electrode, the reference electrode, and the counter electrode are made of gold, titanium, platinum, chromium or aluminum.

15. The apparatus according to claim 2, wherein at least one of the upper layer and the lower layer is made of plastic.

16. The apparatus according to claim 3, wherein at least one of the upper layer and the lower layer is made of plastic.

17. The apparatus according to claim 14, wherein the upper layer and the lower layer are made of plastic.

18. The apparatus according to claim 1, wherein the upper layer or the lower layer is made of plastic.

\* \* \* \* \*